(12) United States Patent
Tornai (10) Patent No.: US 7,393,334 B2
(45) Date of Patent: Jul. 1, 2008

(54) METHOD AND APPLICATION OF A SELF ADHESIVE SPLINT

(76) Inventor: Richard Manuel Tornai, 3125 Avis Way, Pinole, CA (US) 94564

( * ) Notice: Subject to any disclaimer, the term of this patent is extended or adjusted under 35 U.S.C. 154(b) by 371 days.

(21) Appl. No.: 11/102,270

(22) Filed: Apr. 9, 2005

(65) Prior Publication Data
US 2005/0228323 A1    Oct. 13, 2005

Related U.S. Application Data

(60) Provisional application No. 60/561,239, filed on Apr. 10, 2004.

(51) Int. Cl.
*A61F 5/00* (2006.01)
*A61F 13/00* (2006.01)

(52) U.S. Cl. .............. 602/21; 602/5; 602/20; 602/57; 602/64

(58) Field of Classification Search .......... 602/5, 602/20, 21, 41–43, 52, 57, 58, 75; 128/877–879, 128/845, 846; D24/189, 190
See application file for complete search history.

(56) References Cited

U.S. PATENT DOCUMENTS

| | | | | |
|---|---|---|---|---|
| 2,983,272 | A * | 5/1961 | Hunstiger | 128/892 |
| 3,245,406 | A * | 4/1966 | Chardack | 602/79 |
| 5,792,091 | A * | 8/1998 | Staudinger | 602/57 |
| 5,914,125 | A * | 6/1999 | Andrews et al. | 424/443 |
| 6,120,470 | A * | 9/2000 | Bodenschatz et al. | 602/20 |
| 2002/0091348 | A1 * | 7/2002 | Joseph | 602/75 |

* cited by examiner

*Primary Examiner*—Kim M Lewis (57) ABSTRACT

The device is a thin, self-adhesive non-stretch splint, having the capability to flex. This device is intended for the treatment of repetitive stress injuries such as Carpal Tunnel Syndrome with elements that provide user adjustable limitation of movement within acceptable medical parameters. Carpal Tunnel Syndrome symptoms include pain and numbness in the thumb, index, and middle fingers, that are aggravated by compression of the median nerve. This device limits flexion, extension, ulnar and radial deviation movements of the wrist without compressing the median nerve The device limits movement by reducing skin elasticity on the surface skin above or below the wrist and up the forearm. The application provides biomechanical feedback to the wearer in the form of the tugging sensation on the skin around the perimeter of the device assisting the user in maintaining a more neutral wrist position without imposing wrist immobilization. The design elements allow the use of the device in such a manner that produces no additional pressure to the median nerve while in use. Furthermore the method of application provides a means for the user to regulate the amount of wrist movement to provide a greater comfort level while still limiting movement within medically proven parameters. The adhesive nature of the device eliminates the need for external straps that normally wrap completely around the forearm and hand to hold a splint in place. The application of the device limits movement by greatly reducing the ability of the skin to stretch by placing a self-adhesive non-stretch splint directly on the skin. The device, and how it is placed utilizes the wearers skin elasticity to provide biomechanical feedback to the user to promote better wrist posture.

7 Claims, 5 Drawing Sheets

METHOD AND APPLICATION OF A SELF ADHESIVE SPLINT

I wish to claim priority filing date of Apr. 10, 2004 from provisional application USPTO Ser. No. 60/561239.

FIELD OF THE INVENTION

This invention relates to the use of rigid and semi rigid splints for the treatment and prevention of repetitive stress injuries specifically Carpal Tunnel Syndrome.

DESCRIPTION OF THE PRIOR ART

Rigid and semi rigid splints are commonly used in the treatment of repetitive stress injuries. Carpal Tunnel Syndrome (CTS) is categorized as a repetitive stress injury. CTS is caused due to compression of the median nerve located under the transverse carpal ligament in the center of the wrist in a small channel called the Carpal Tunnel. Repetitive movement and poor wrist posture can cause the tissue around the median nerve to swell thereby compressing it. The symptoms usually consist of pain and numbness in the thumb, index, and middle fingers.

Repetitive stress injuries such as CTS can be easily aggravated by flexing or extending wrist movements for prolonged periods of time. The function of a splint is to partially or completely restrict wrist flexion and extension movements thereby reducing median nerve compression. Individuals who wear wrist splints can reduce symptoms.

Current splint technology contains two major flaws. First, they completely cover and in many cases apply additional pressure on the median nerve. Applying unnecessary pressure to the median nerve actually aggravates the condition. Secondly, the use of rigid elements sewn into the fabric and fastened with latch hoop (Velcro) straps to completely immobilize wrist movement can also generate additional pressure to the median nerve with normal use. Due to the highly restrictive nature of rigid splints secondary injuries to the thumb joints, arm and shoulder are common. Typically these devices are bulky and extremely conspicuous. In some cases individuals using wrist splints have difficulty wearing existing clothing due to the bulky nature of the device. The intrusive nature of the design can also be a deterrent to its use. Medical research indicates that complete wrist immobilization is unnecessary and in some cases undesirable. These factors contribute to borderline sufferers not wearing splints thereby aggravating their conditions. A device that provides support within medically proven parameters, while eliminating the uncomfortable obtrusive nature of existing splints, would encourage more people to wear them thus slowing the progression of CTS.

Carpal Tunnel Syndrome is often aggravated while sleeping. During sleep individuals can easily place the wrist in a hyper flexed position (downward movement) that compresses the median nerve to such an extent that they can be awakened with pain and numbness. Both rigid and semi rigid splints can be worn at night to reduce these symptoms however due to the nature of their construction they can be exceptionally uncomfortable and lead to interrupted sleep patterns. Interrupted sleep patterns are the primary reason borderline CTS suffers undergo surgical treatment. Reducing nighttime CTS pain symptoms would significantly lessen the need for costly surgical procedures.

SUMMARY OF THE INVENTION

The present invention addresses the need to restrict flexion, extension, radial and ulnar deviation movements in the wrist and hand while reducing pressure on the median nerve and being more comfortable for the user to wear. Complete restriction that is imposed on wrist movement by most existing devices is unnecessary. Training individuals to become aware of wrist movement and posture can help to reduce symptoms. Additionally, some form of wrist position feedback can contribute greatly to reducing symptoms.

Current technology restricts wrist flexion, extension ulnar, and radial movement by severely restricting and in some cases immobilizing any range of motion. Medical research indicates that up to 15 degrees of flexion measured from a neutral wrist position, and 15 degrees of extension also measured from a neutral wrist position can be tolerated without irritating the median nerve, provided that minimal pressure is applied to the median nerve in the process. Ulnar and radial deviation can be as much as 5 degrees in either direction without further aggravating the condition.

Limited wrist movement is possible without rigid or bulky means by reducing the natural ability of the skin to stretch in the general area surrounding the wrist. This is accomplished by using a self-adhesive splint that is flexible but will not stretch. By applying the splint on top of the hand and slightly down the forearm and another strip on the palm side of the hand also extending down the forearm is an effective method of limiting unwanted wrist movement without immobilizing for two reasons. First, it can reduce overall elasticity of the skin allowing for more natural movement with better overall wrist posture. Second, the skin surrounding the perimeter of the device becomes more sensitive to movement. The enhanced sensitivity provides a biomechanical feedback in the form of a gentle tug on the skin providing a stretching sensation on the skin when the wrist begins to flex, extend or move on the radial or ulnar axis outside of recommended parameters. The adhesive splint design elements effectively limit wrist movement while making application and use of the device easy and comfortable. The size and shape of the splint is designed to be as small as possible, in terms of both surface area and thickness of the device, to reduce skin stretch while applying a minimum amount of adhesive material to the skin making it strong yet more comfortable to wear. The design of the adhesive splint is such that no additional pressure is applied over the median nerve reducing splint induced median nerve compression. The design also includes elements to reduce the possibility of the device catching on clothing or bedding, or interfering with wearing regular clothing or protective clothing.

DETAILED DESCRIPTION OF THE PREFERRED EMBODIMENT

Figures 1, 2:
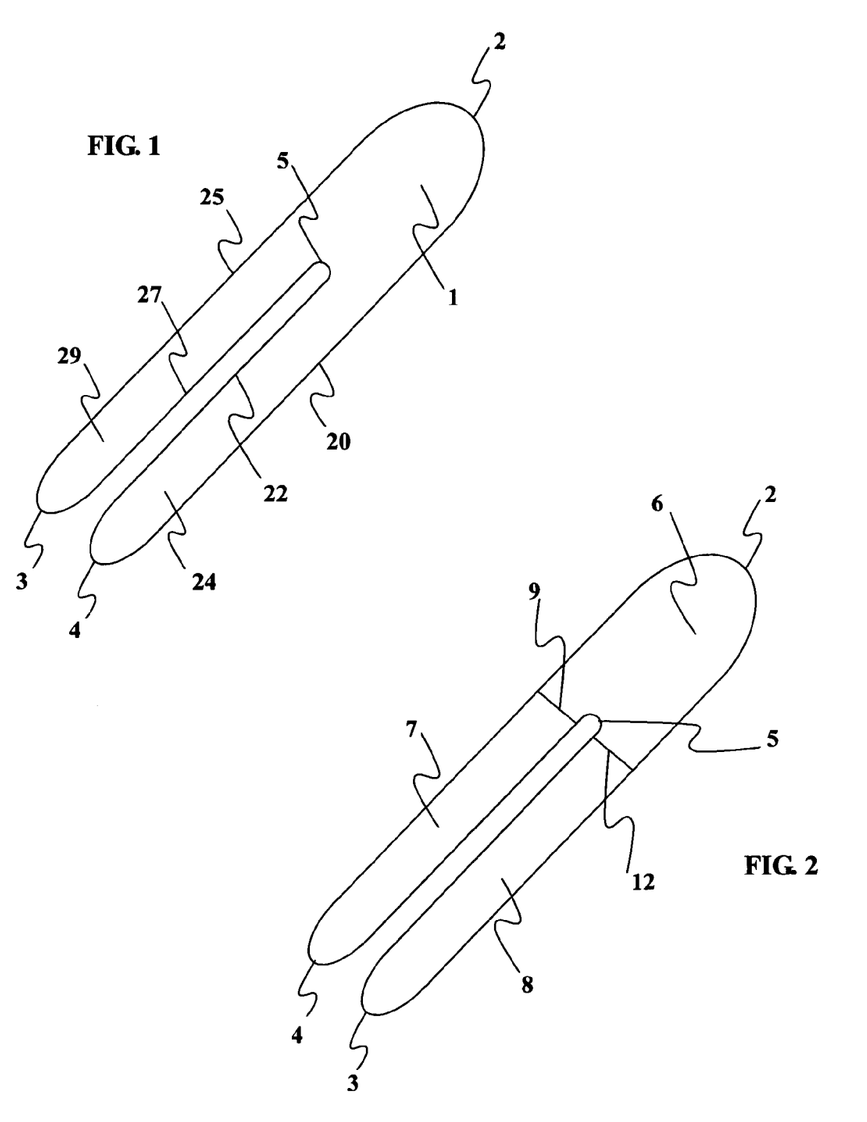
FIG. 1 Top view the device
FIG. 2 Bottom view of the device showing three sections of the removable liner and the protective liner cut separating the three sections.

The present invention consists of a thin, non-stretch, self-adhesive splint device illustrated in FIG. 1 (top view) and method of placing the splint in such a way as to maintain proper wrist position by limiting the ability of the skin surrounding the wrist and forearm to stretch. Limiting the skin from stretching reduces hand flexion and extension movements as well as ulnar and radial deviation. The limitation of movement is accomplished by reducing skin elasticity on the skin surface area generally surrounding the wrist without applying additional pressure to the median nerve.

Placement of two devices, on either side of the wrist, is required to reduce both flexion and extension movement. The method of application of the device on top of the wrist FIG. 4, when in the pronated position (palm down), limits flexion. A second device properly applied on the bottom of the wrist FIG. 7, in the supinated position (palm up), limits extension. Ulnar and radial deviation movements are limited by adjusting the placement of the two forearm elements 24, 29.

Limiting only flexion movement is an effective method for treating nighttime CTS symptoms. Therefore the application of two devices is not necessary when addressing sleep related symptoms. The application of two devices to limit flexion, extension, ulnar, and radial movement is preferred for daytime use.

Limiting the ability of the skin to stretch provides movement limitations instead of immobilization. Immobilizing the wrist can cause the user to over compensate normal movements resulting in secondary injuries to the thumb joints, arm, shoulder, and neck.

Figure 3:
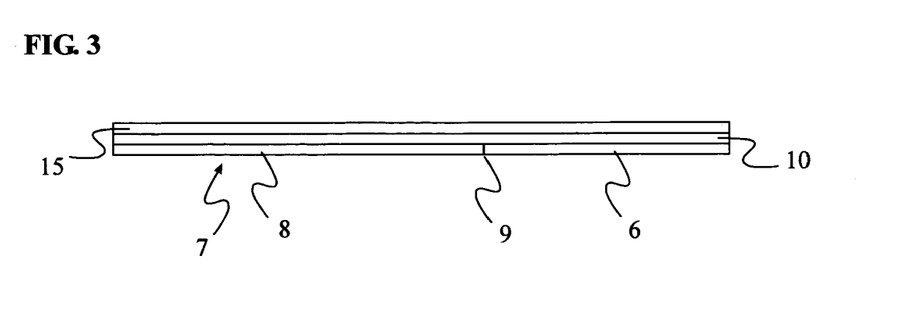
FIG. 3 Expanded side view (not to scale) of the device showing the arrangement of the layers comprising the device.

FIG. 1 shows a top view of the self-adhesive splint device with the hand element 1 and the two forearm elements 24, 29. FIG. 3 is an expanded cross section view of the splint (not to scale) illustrating the three layers that comprise the device. The top layer is a non-stretch backing 15 that is very thin and coated on one side with an adhesive 10 creating the second layer. The other side of the adhesive layer 10 is covered with protective removable liners 6, 7, 8, creating layer three as shown in FIG. 2). These materials are similar to those used on lined medical grade adhesive tape. The thin backing layer 15 is constructed of non-woven materials that can bend but do not stretch on any axis. The overall device is die cut out of a single piece creating the overall shape of the device FIG. 1.

The ends of the device are cut into three arcs 2, 3, 4. The arc shape 2 around the hand element 1 is cut to maximize the adhesive contact area on either the palm side or back of the hand while providing a smooth transition to the outside perimeter of the device, 20, 25. The arc shapes 3,4 on the ends of the two forearm elements 24, 29 also provide a smooth transition to the outside perimeter of the device, 20, 25 and inside edges 22, 27 separating the two forearm elements 24, 29 from each other. The transition arc 5, between the two forearm elements 24, 29 provides a smooth transition where they join to the hand element 1. The distance between the forearm elements 24, 29 is adjusted to control ulnar and radial deviation. The shape of the transition (cut) arc 5, reduces the possibility of the backing layer 15 teasing when force is applied between the hand element 1 and either of the two forearm elements 24, 29 when the user attempts flexion, extension movement, ulnar or radial deviation movements.

The arc shapes 2, 3, 4, 5 also eliminate angular edges that can cause the device to adhere to clothing or bedding resulting in inadvertent removal of the device.

The protective liner side of the device FIG. 2 illustrates where the liner is cut 9, 12 creating three removable liner sections 6, 7, 8. The liner cuts 9, 12 sever the liner sections 6, 7, 8 from each but do not penetrate the adhesive layer 10, and do not penetrate the backing layer 15. The purpose of the liner cuts 9, 12 is to provide easier application of the device by removing one liner section 6,7,8 at the time when applying to the hand. Reducing exposure of the adhesive under the protective liner sections 6, 7, 8, is necessary to ensure proper application. Because of the ultra thin nature of the device, removing the entire liner as one piece would interfere with an overall smooth, consistent application of the device on to the skin.

Figure 4:
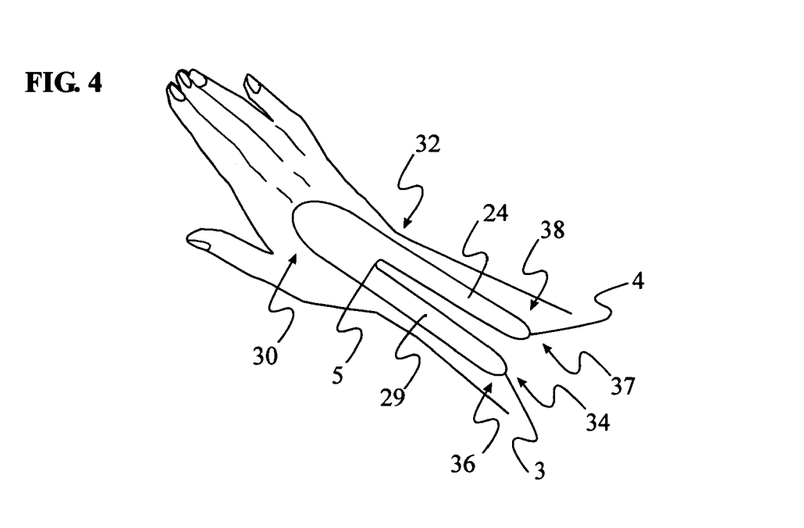
FIG. 4 Placement of the device on the back of the hand to restrict flexion.
Figure 5:
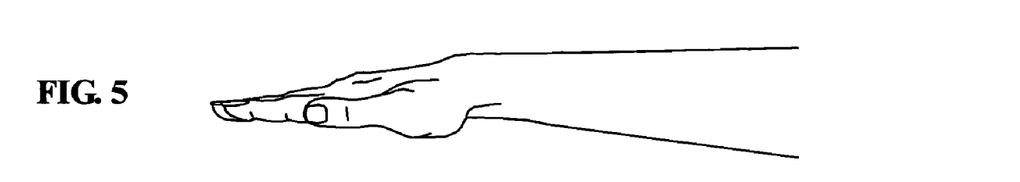
FIG. 5 Side view of the hand in a neutral position

Applying the device to reduce flexion starts by placing the hand in the pronated (palm down) position FIG. 4 while maintaining a neutral wrist position 0 (zero) degrees of extension as shown in FIG. 5. The protective liner section 6 is removed from hand element 1. The hand element 1 is then placed, with the adhesive side on the skin FIG. 4 on and near the center of the back of the hand 30 with the transition cut 5 positioned just in front of the wrist joint 32. Pressure is applied to the back of the hand element 1 to assure that the entire surface of the hand element 1 makes complete contact with the skin on the back of the hand in a smooth consistent manner. The hand is then extended FIG. 6 in a positive direction, between +5 (positive five) and +45 (positive forty-five) degrees, from the neutral 0 (zero) degree position shown in FIG. 5. The amount of positive extension will vary depending on the elasticity of the users skin occupying the area to be covered by the device. With the hand in the positive extension position FIG. 6 the protective lining 8 is removed from the first forearm element 29 exposing the adhesive layer 10. After the adhesive layer 10 is exposed, tension is maintained on the end of the first forearm element 29 by the user holding on to the arched end 3. The arched end 3 is then placed on the skin FIG. 6 in the position 34 (side view) and FIG. 4 position 34 (top view). Pressure is then applied to length of the first forearm element 29 so that the adhesive 10, makes complete contact with the skin on the back of the forearm in a smooth consistent manner.

Ulnar deviation can be reduced by moving the contact point FIG. 4 of arch 3 from point 34, closer to the radial side of the forearm near area 36. The open space between the two forearm elements 24, 29 allows them to be placed so as to better conform to the natural shape of the ulnar and radial sides of the forearm.

Figure 6:
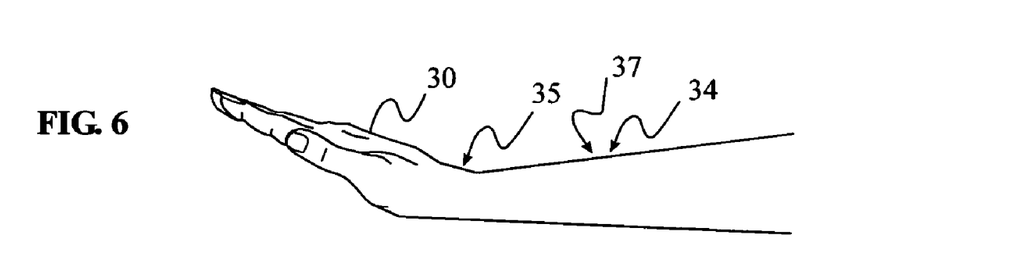
FIG. 6 Side view of the hand with positive extension.

This process is repeated for the placement of the second forearm element 24 by maintaining the extended hand position FIG. 6 in a positive direction, between +5 (positive five) and +45 (positive forty-five) degrees, from the neutral 0 (zero) degree position shown in FIG. 5. While the hand remains in the positive extension position FIG. 6, the protective lining 7, is removed from the adhesive layer 10 on the second forearm element 24. After the adhesive layer 10 is exposed by removing the liner 7, tension is maintained on the end of the second forearm element 24 by the user holding on to the arched end 4. The arched end 4 is then placed on the skin FIG. 4 in the position 37. Pressure is then applied to length of the second forearm element 24 so that the adhesive 10, makes complete contact with the skin on the back of the forearm in a smooth consistent manner.

Radial deviation can be reduced by moving the contact point of the arch shape 4 from point 37, closer to the ulnar side of the arm near area 38. The open space between the two forearm elements 24 and 29 allows them to be placed so as to better conform to the natural shape of the ulnar and radial sides of the forearm.

By pressing the two forearm elements 24, 29 onto the area of loose skin on the top of the wrist area 35, the non-stretch nature of the device FIG. 1 provides a large area on the back of the hand and forearm that will not stretch. The effect of the device FIG. 1 and how it is placed on the back of the hand and forearm is that wrist flexion is significantly limited by reducing skin elasticity in the area occupied by the device.

Figure 9:
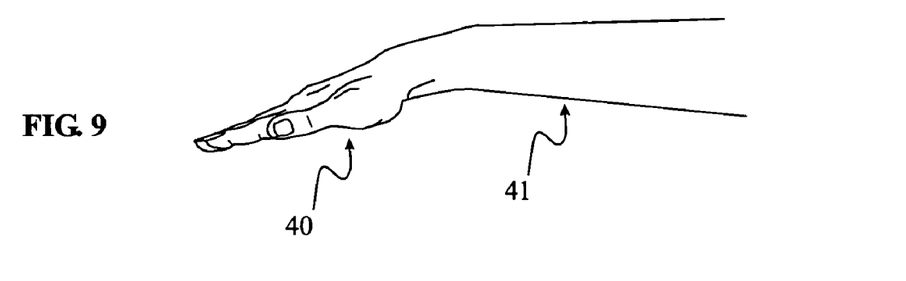
FIG. 9 Test position to check flexion limits on the hand when the wrist is limp.

Correct application of the device to limit flexion is checked FIG. 9 by allowing the wrist to go limp (relaxed) in the pronated position. The device has been correctly placed when the hand is relaxed and the angle of positive flexion, measured between the forearm 41 and the hand 40, is less than +15 (positive fifteen) degrees when measured from the neutral 0 (zero) degree position FIG. 5. One device is applied on pronated (top side of the hand) to reduce flexion while sleeping.

Figure 7:
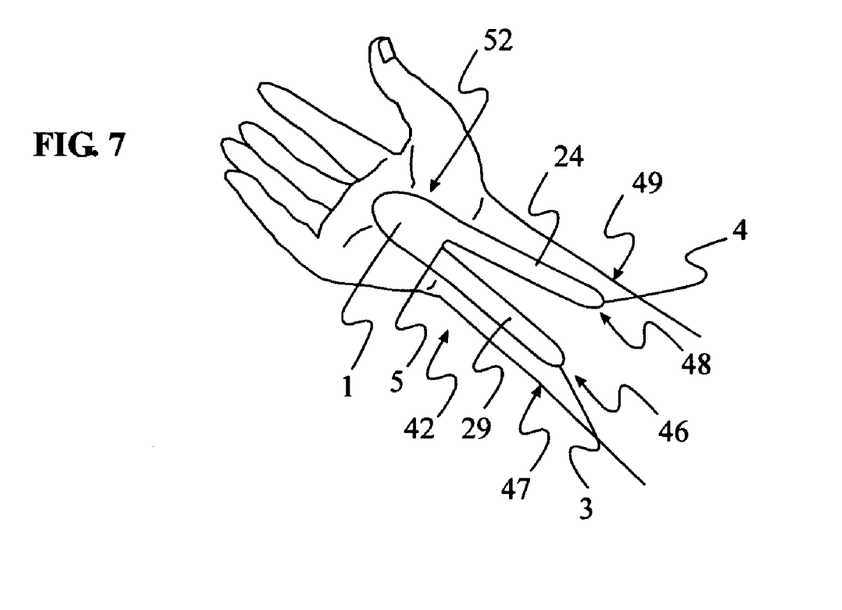
FIG. 7 Placement of the device on the palm side of the hand to restrict extension.
Figure 8:
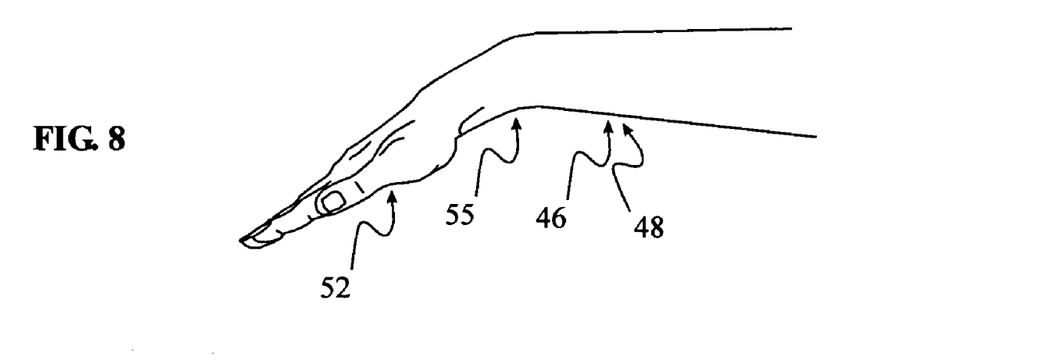
FIG. 8 Side view of the hand with positive flexion.

Applying the device to reduce extension starts by placing the hand in the supinated (palm up) position FIG. 7 while maintaining a neutral wrist position 0 (zero) degrees of extension shown in FIG. 5. The protective liner 6, is removed from the hand element 1. The hand element 1 is then placed, with the adhesive side on the skin FIG. 7 on the palm of the hand 52 so that the transition cut 5 is positioned just in front of the wrist joint 42 without covering the Carpal Tunnel area. Pressure is applied to the back of the hand element 1 to assure that the entire surface of the hand element 1, makes complete contact with the skin on the palm of the hand in a smooth consistent manner. The hand is then flexed as shown in FIG. 8 in a positive direction, between +5 (positive five) and +45 (positive forty-five) degrees, from the neutral 0 (zero) degree position shown in FIG. 5. The amount of positive flexion will vary depending on the elasticity of the users skin occupying the area to be covered by the device. With the hand in the positive flexion position FIG. 8, the protective lining 8, is removed from the first forearm element 29 exposing the adhesive layer 10. After the adhesive layer 10 is exposed, tension is maintained on the end of the first forearm element 29 by the user holding on to the arched end 3. The arched end 3 is then placed on the skin FIG. 7 in the position 46. Pressure is then applied to length of the first forearm element 29 so that the adhesive 10, makes complete contact with the skin on the back of the forearm in a smooth consistent manner.

Radial deviation can be reduced by moving the contact point of arch 3 from point 46, closer to the ulnar side of the forearm near area 47. The open space between the forearm elements 24, 29 allows them to be placed so as to better conform to the natural shape of the ulnar and radial sides of the forearm.

This process is repeated for the placement of the second forearm element 24 by maintaining the flexed hand position FIG. 8 in a positive direction, between +5 (positive five) and +45 (positive forty-five) degrees, from the neutral 0 (zero) degree position shown in FIG. 5. While the hand remains in the positive flexion position FIG. 8, the protective lining 7, is removed from the adhesive layer 10 on the second forearm element 24. After the adhesive layer 10 is exposed, tension is maintained on the end of the second forearm element 24 by the user holding on to the arched end 4. The arched end 4 is then placed on the skin FIG. 7 in the position 48. Pressure is then applied to length of the second forearm element 24 so that the adhesive 10, makes complete contact with the skin on the palm side of the forearm in a smooth consistent manner.

Ulnar deviation can be reduced by moving the contact point of the arch shape 4 from point 48, closer to the radial side of the forearm near area 49. The open space between the two forearm elements 24, 29 allows them to be placed so as to better conform to the natural shape of the ulnar and radial sides of the forearm.

By pressing the two forearm elements 24, 29 onto the area of loose skin under the wrist area 55, the non-stretch nature of the device FIG. 1 provides a large area on the palm side of the hand and forearm that will not stretch. The effect of the device FIG. 1 and how it is placed on the palm of the hand and forearm is that wrist extension is significantly limited by reducing skin elasticity in the area occupied by the device.

Figure 10:
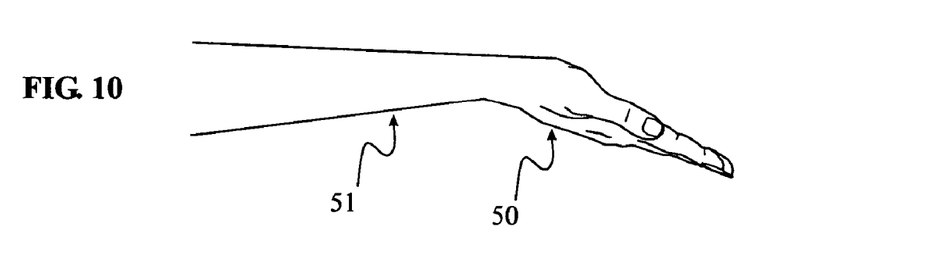
FIG. 10 Test position to check extension limits on the hand when the wrist is limp.

Correct application of the device to restrict extension is checked FIG. 10 by allowing the wrist to go limp (relaxed) in the supinated position. The device has been correctly placed if when the hand is relaxed and the angle of positive flexion measured between the forearm 51, had the hand, 50 is less than +15 (positive fifteen) degrees when measured from the neutral 0 (zero) degree position FIG. 5. Two devices are applied one on the pronated FIG. 4 (top of hand) and a second on the supinated FIG. 7 (palm side) during the day to limit both flexion and extension.

The device is constructed from a single piece of thin non-stretch, adhesive coated material similar to a non-woven medical tape. There is virtually no bulk associated with wearing the device. This creates greater comfort while effectively limiting movement within acceptable parameters, especially during sleep. The design of the device provides the functionality of rigid or semi rigid splints without the negative side effects, specifically, discomfort when worn and increased median nerve pressure.

The application of the device FIG. 1 provides biomechanical feedback to the wearer in the form of the tugging sensation on the skin around the perimeter of the device assisting the user in maintaining a more neutral wrist position without imposing wrist immobilization.

What is claimed is:

1. A method of limiting wrist flexion, comprising the steps of:
   I. providing an adhesive wrist splint for restricting movement of the wrist, consisting of: a non-stretch backing having a first end and a second end and an adhesive coating on one side of the backing extending from the first end to the second end; protective removable liners covering the adhesive coating; said non-stretch backing material capable of flexing to conform to the form of the extremity to which it is applied; said non-stretch backing material is generally shaped as an elongated rectangle having a gap therein that partially extends the length of the backing material, the gap defines two elongated segments spaced away from and opposite one another and a third segment positioned adjacent the elongated segments, the third segment having a length smaller than the two elongated segments;
   II. positioning the hand in a neutral position relative to the forearm;
   III. placing the third segment of the non-stretch backing on the back of a hand just behind the knuckles leaving the two elongated segments positioned over the forearm and unattached;
   IV. moving the hand position to a positive extension between five and forty-five degrees;
   V. applying tension to the two elongated segments of the non-stretch backing and applying the two elongated segments to the forearm;
   VI. applying pressure to the two elongated elements to secure the adhesive to the skin, substantially reducing the ability of the skin to stretch, limiting flexion; and VII. allowing the wrist to relax observing that the amount of flexion does not exceed positive position of fifteen degrees and repositioning if necessary.

2. A method of limiting wrist extension, comprising the steps of:
   I. providing an adhesive wrist splint for restricting movement of the wrist, consisting of: a non-stretch backing having a first end and a second end and an adhesive coating on one side of the backing extending from the first end to the second end; protective removable liners covering the adhesive coating; said non-stretch backing material capable of flexing to conform to the form of the extremity to which it is applied; said non-stretch backing material is generally shaped as an elongated rectangle having a gap therein that partially extends the length of the backing material, the gap defines two elongated segments spaced away from and opposite one another and a third segment positioned adjacent the elongated segments, the third segment having a length smaller than the two elongated segments;
   II. positioning the hand in a neutral position relative to the forearm;
   III. placing the third segment of the non-stretch backing near the center of the palm leaving the opposite end positioned over the forearm and unattached;
   IV. moving the hand position to a positive flexion between five and forty-five degrees;
   V. applying tension to the free end of the non-stretch adhesive coated material and applying the end to the forearm;
   VI. applying pressure to the two elongated segments to secure the adhesive to the skin, substantially reducing the ability of the skin to stretch limiting extension and;
   VII. allowing the wrist to relax observing that the amount of extension does not exceed positive position of fifteen degrees and repositioning if necessary.

3. A method of applying an adhesive wrist splint for restricting movement of the wrist, consisting of: a non-stretch backing having a first end and a second end and an adhesive coating on one side of the backing extending from the first end to the second end; protective removable liners covering the adhesive coating; said non-stretch backing material capable of flexing to conform to the form of the extremity to which it is applied; said non-stretch backing material is generally shaped as an elongated rectangle having a gap therein that partially extends the length of the backing material, the gap defines two elongated segments spaced away from and opposite one another and a third segment positioned adjacent the elongated segments, the third segment having a length smaller than the two elongated segments, wherein the wrist splint is shaped to provide a smooth transition around the parameter and, the protective removable liners covering the adhesive coating are separated into section so as to allow independent removal of the protective liner sections, to reduce radial deviation, comprising the steps of:
   I. positioning the hand in a neutral position relative to the forearm;
   II. removing the protective liner from the third segment and positioning the third segment near the center of the palm leaving the two elongated segments positioned over the forearm and unattached;
   III. moving the hand position to a positive flexion between five and forty-five degrees;
   IV. removing the protective liner from one elongated segment positioned closest to the ulnar, applying tension to the free end and applying the end nearer to the ulnar side of the forearm;
   V. removing the protective liner from the other elongated segment and applying it nearer to the radial side of the forearm; and
   VI. applying pressure to the two elongated segments to secure the adhesive to the skin, substantially reducing the ability of the skin to stretch in radial movement, thereby reducing radial deviation.

4. A method of applying an adhesive wrist splint for restricting movement of the wrist, consisting of: a non-stretch backing having a first end and a second end and an adhesive coating on one side of the backing extending from the first end to the second end; protective removable liners covering the adhesive coating; said non-stretch backing material capable of flexing to conform to the form of the extremity to which it is applied; said non-stretch backing material is generally shaped as an elongated rectangle having a gap therein that partially extends the length of the backing material, the gap defines two elongated segments spaced away from and opposite one another and a third segment positioned adjacent the elongated segments, the third segment having a length smaller than the two elongated segments, wherein the wrist splint is shaped to provide a smooth transition around the parameter and, the protective removable liners covering the adhesive coating are separated into section so as to allow independent removal of the protective liner sections to reduce ulnar deviation comprising the steps of:
   I. positioning the hand in a neutral position relative to the forearm;
   II. removing the protective liner from the third segment and positioning the third section near the center of the palm leaving the two elongated segments positioned over the forearm and unattached,
   III. moving the hand position to a positive flexion between five and forty-five degrees,
   IV. removing the protective liner from one of the elongated segments positioned closest to the radius, applying tension to said one of the elongated segments and applying said one of the elongated segments nearer to the radial side of the forearm;
   V. removing the protective liner from the other elongated segment, applying tension to said other elongated segment and applying it nearer to the ulnar side of the forearm, and
   VI. applying pressure to the elongated segments to secure the adhesive to the skin substantially reducing the ability of the skin to stretch in ulnar movement, thereby reducing ulnar deviation.

5. A method of applying an adhesive wrist splint for restricting movement of the wrist, consisting of: a non-stretch backing having a first end and a second end and an adhesive coating on one side of the backing extend from the first end to the second end; protective removable liners covering the adhesive coating; said non-stretch backing material capable of flexing to conform to the form of the extremity to which it is applied; said non-stretch backing material is generally shaped as an elongated rectangle having a gap therein that partially extends the length of the backing material, the gap defines two elongated segments spaced away from and opposite one another and a third segment positioned adjacent the elongated segments, the third segment having a length smaller than the two elongated segments, wherein the wrist splint is shaped to provide a smooth transition around the parameter and, the protective removable liners covering the adhesive coating are separated into section so as to allow independent removal of the protective liner sections to reduce extension and reduce pressure on the median nerve comprising the steps of:

I. positioning the hand in a neutral position relative to the forearm;
II. removing the protective liner from the third segment and positioning the third segment near the center of the palm leaving the the two elongated segments positioned over the forearm and unattached;
III. moving the hand position to a positive flexion between five and forty-five degrees;
IV. removing the protective liner from one of the elongated segments positioned closest to the radius, applying tension to said one of the elongated segments and applying said one of the elongated segments to the radial side of the forearm avoiding placing said one of the elongated segment directly over the median nerve region;
V. applying pressure to said one of the elongated segments to secure the adhesive to the skin;
VI. removing the protective liner from the other elongated segment opposing the previous application, applying tension to the other elongated segment and applying the other elongated segment closest to the ulnar side of the forearm avoiding placing the other elongated segment directly over the median nerve region; and
VII. applying pressure to the other elongated segment to secure the adhesive to the skin, substantially reducing the ability of the skin to stretch, thereby reducing extension movement without applying additional pressure to the area over the median nerve.

6. The method of claim 1, 2, 3, 4 or 5 wherein, the step of applying tension to the two elongated segments comprises applying tension to the elongated segments individually.

7. The method of claim 1, 2, 3, 4 or 5, wherein, the removable protective liners are removed one at a time before placing the segments on the hand and forearm.

* * * * *